US010401082B2

(12) United States Patent
Coradetti et al.

(10) Patent No.: US 10,401,082 B2
(45) Date of Patent: Sep. 3, 2019

(54) TRACKING OF SAMPLE BOXES USING ENERGY HARVESTING

(71) Applicant: BioTillion, LLC, Skillman, NJ (US)

(72) Inventors: Thomas Coradetti, Belle Mead, NJ (US); Hananel Davidowitz, Princeton, NJ (US); Theodore Altman, East Windsor, NJ (US)

(73) Assignee: BioTillion, LLC, Skillman, NJ (US)

( * ) Notice: Subject to any disclaimer, the term of this patent is extended or adjusted under 35 U.S.C. 154(b) by 1190 days.

(21) Appl. No.: 14/184,815

(22) Filed: Feb. 20, 2014

(65) Prior Publication Data

US 2014/0230472 A1    Aug. 21, 2014

Related U.S. Application Data

(60) Provisional application No. 61/766,748, filed on Feb. 20, 2013.

(51) Int. Cl.
| | |
|---|---|
| *G06F 19/00* | (2018.01) |
| *F25D 29/00* | (2006.01) |
| *A01N 1/00* | (2006.01) |
| *G06Q 10/08* | (2012.01) |
| *A01N 1/02* | (2006.01) |
| *F25D 11/04* | (2006.01) |
| *F25D 13/02* | (2006.01) |
| *F25D 25/02* | (2006.01) |

(52) U.S. Cl.
CPC ............ *F25D 29/008* (2013.01); *A01N 1/00* (2013.01); *A01N 1/0242* (2013.01); *A01N 1/0252* (2013.01); *A01N 1/0268* (2013.01); *F25D 29/00* (2013.01); *G06Q 10/087* (2013.01); *F25D 11/04* (2013.01); *F25D 13/02* (2013.01); *F25D 25/02* (2013.01); *F25D 2500/06* (2013.01); *F25D 2700/08* (2013.01)

(58) Field of Classification Search
CPC ..... G06Q 10/087; G06Q 20/203; G06Q 20/32
USPC .............. 235/385, 492, 462.46, 472.02
See application file for complete search history.

(56) References Cited

U.S. PATENT DOCUMENTS

| | | | | |
|---|---|---|---|---|
| 3,896,958 | A  * | 7/1975 | Robbins ............... | B65D 50/061 |
| | | | | 215/211 |
| 5,777,303 | A  * | 7/1998 | Berney ................. | B01L 3/5453 |
| | | | | 235/375 |
| 6,831,552 | B2 * | 12/2004 | Lin ........................ | B65D 41/34 |
| | | | | 215/200 |
| 2003/0095253 | A1 * | 5/2003 | Chow ..................... | B65D 1/02 |
| | | | | 356/240.1 |

(Continued)

*Primary Examiner* — Daniel St Cyr
(74) *Attorney, Agent, or Firm* — Mendelsohn Dunleavy, P.C.; Steve Mendelsohn

(57) ABSTRACT

In one embodiment, a freezer system has one or more shelves, each shelf has shelf electronics and can receive one or more racks, each rack has rack electronics and one or more cells for receiving one or more boxes of samples, each box has one or more RFID tags. Freezer electronics communicate with the outside world and with each set of shelf electronics. Each set of rack electronics communicates wirelessly with the corresponding set of shelf electronics and with the corresponding box RFID tags. Power for the rack electronics is derived from wireless signals from the shelf electronics. The freezer system can detect the presence of racks on shelves and boxes on racks to track the location and the orientation of each received box.

33 Claims, 10 Drawing Sheets

(56) References Cited

U.S. PATENT DOCUMENTS

| | | | | |
|---|---|---|---|---|
| 2006/0245865 A1* | 11/2006 | Babson | ............... | G01N 35/025 |
| | | | | 414/331.01 |
| 2007/0205126 A1* | 9/2007 | Elsener | .................... | B01L 9/52 |
| | | | | 206/456 |
| 2008/0106388 A1* | 5/2008 | Knight | ............... | A61M 5/31511 |
| | | | | 340/10.42 |
| 2009/0234839 A1* | 9/2009 | Angell | ................... | G06Q 10/04 |
| 2009/0242446 A1* | 10/2009 | Abbott | ................ | B65D 25/205 |
| | | | | 206/459.5 |
| 2010/0328037 A1* | 12/2010 | Thomas | ................. | F25D 29/00 |
| | | | | 340/10.1 |
| 2011/0199187 A1* | 8/2011 | Davidowitz | ........... | B01L 3/545 |
| | | | | 340/10.1 |

\* cited by examiner

TRACKING OF SAMPLE BOXES USING ENERGY HARVESTING

CROSS-REFERENCE TO RELATED APPLICATIONS

This application claims the benefit of the filing date of U.S. provisional application No. 61/766,748, filed on Feb. 20, 2013, the teachings of which are incorporated herein by reference in their entirety.

STATEMENT REFARDING FRDERALLY SPONSORED RESEARCH OR DEVELOPMENT

The Government of the United States of America has rights in this invention pursuant to National Institutes of Health (NIH) Grant Nos. 1R43RR024787-01, 3R43RR024787-01S1, 2R44RR024787-02A1, and 5R44RR024787-03 awarded by the U.S. Department of Health and Human Services.

BACKGROUND

Field of the Invention

The present invention relates to radio-frequency identification (RFID) and, more specifically but not exclusively, to systems for locating RFID-tagged objects.

Description of the Related Art

This section introduces aspects that may help facilitate a better understanding of the invention. Accordingly, the statements of this section are to be read in this light and are not to be understood as admissions about what is prior art or what is not prior art.

Tens of millions of new biological samples are being collected and stored annually in a variety of settings including clinical trials at pharmaceutical companies, universities, and hospitals, diagnostic testing and research, forensic samples from crime or disaster scenes, databases of criminal populations, national genetic data bases, genetic studies, etc. Many of these samples are stored in biobanks at ultra low temperatures.

Today, tracking these samples requires meticulous record keeping. If samples are spilled, then they have to be replaced in their former location or a recording has to be made of where they are. Either process takes time and inevitably warms the samples causing degradation. In addition, samples that are misplaced are difficult or impossible to locate.

In some settings, such as those that deal with dangerous samples or in the case of forensic evidence, all samples must be accounted for at all times. Therefore, inventories are carried out on a regular basis. Performing inventories by hand can be very costly. In addition, some samples can be very expensive or impossible to replace.

BRIEF DESCRIPTION OF THE DRAWINGS

Other embodiments of the invention will become more fully apparent from the following detailed description, the appended claims, and the accompanying drawings in which like reference numerals identify similar or identical elements.

FIGS. 6(A) and 6(B) show simplified block diagrams of portions of an exemplary implementation of the freezer system of FIG. 1, while FIG. 6(C) shows a figurative view of a multi-component rack antenna for that system;

DETAILED DESCRIPTION

Figure 1:
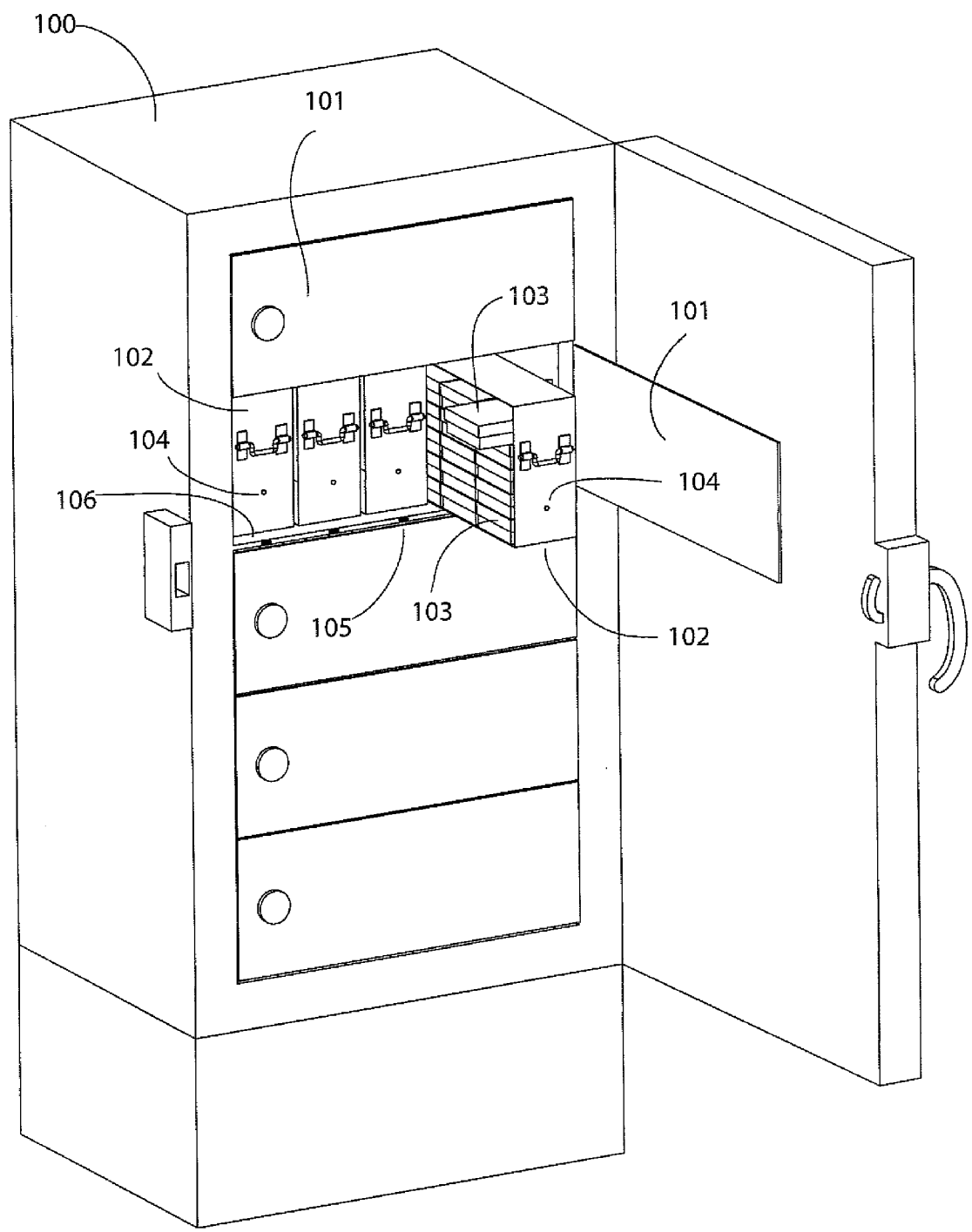
FIG. 1 shows a perspective view showing the main system components of a freezer according to one embodiment of the disclosure.

One method that can be used to address these problems is a wireless RFID-based tracking system for individual vials or boxes in a biobank. Inventories, which currently require hundreds of person hours, could be done in seconds. Lost samples will be a thing of the past, since any sample anywhere in the freezer can easily be found by simply doing a software search of the freezer database. The freezer database is updated automatically, as often as desired. Every time the freezer database is updated, the location of every sample and/or box of samples is read and its location is entered into the database.

Locating every box or vial in the freezer can be achieved using electronics that can interact with RFID-tagged vials and boxes. However, the internal components in a freezer can be moved from place to place. Boxes are stored in racks that can be moved from shelf to shelf in the same freezer or between freezers. Vials, in turn, are stored in boxes that can be moved between racks. So, a method is needed to transmit and receive data and power in the freezer in such a way that the components can be moved around freely and then automatically be located. Using wired connections is not an option because of the buildup of ice in the freezer. A wireless method of sending data and power between the various components is needed.

We describe here how such a system can be designed. The problem we address here is how to locate a specific item in a collection of items. By "specific item," we refer to a discrete physical entity, not a type of entity. So, in the example of a vending machine, we refer to a specific candy bar, not a specific type of candy bar.

We discuss in detail the example of a freezer of biological samples where the samples are stored in sample boxes. In this situation, plugging items in and out of sockets to connect electronics is not practical because of ice and frost.

By "board," we refer to a printed circuit board or PCB. By "RF," we mean radio frequency, and, by "cell," we mean any one of the possible box locations in the rack. So, for example, a 3 row by 5 column rack will have 15 cells. By "selection state," we refer to a collection of bits in a counter, shift register, memory device, etc., that defines a unique signal path through the multiplexer tree. Sometimes "mux" is used in place of multiplexer.

The subject matter of this application is related to the subject matter of U.S. Pat. Nos. 8,346,382 and 8,378,827 and U.S. patent application Ser. Nos. 13/026,359, 13/437,980, and 13/684,653, the teachings of all of which are incorporated herein by reference in their entirety.

Our objective is to locate a specific sample box in the freezer. These boxes are typically stored in removable sub-units called racks that contain multiple boxes (usually up to 35 boxes per rack). But the inventions presented here could be applied to other storage systems as well, such as Formalin-Fixed, Paraffin-Embedded (FFPE) tissue blocks and non-biological storage systems, such as, a warehouse housing hazardous materials where making or breaking a physical electrical connection can be dangerous. While recognizing the utility of this technology in other applications, we will discuss a freezer-based system since that is the most technically challenging. Where appropriate, in an FFPE storage system, for example, wired (i.e., ohmic) connections can be used in some places when frost and ice are not an issue.

We discuss the details for locating a removable box placed in a removable rack in a sample repository where the items to be located have defined, possible locations and are tagged using RFID tags. This might be a biological sample repository such as a −80° C. freezer, although the ideas apply to colder (e.g., liquid nitrogen freezers at −196° C.) or warmer (e.g., −20° C.) freezers and even room-temperature repositories. Obviously, any electronics in any of the embodiments discussed here would have to operate at their local temperature.

FIG. 1 shows a perspective view showing the main system components of a freezer 100 according to one embodiment of the disclosure. The freezer 100 has 5 shelves 106, each of which is protected by a frost door 101. On each shelf are 5 racks 102 containing boxes 103 for storing vials (not shown). Indicator lights 104 and 105 will be further discussed below. Typical mechanical freezers like the one shown in FIG. 1 can vary widely in how they are organized internally. A typical freezer can have on the order of 5 shelves, tens of racks, hundreds of boxes, and tens of thousands of vials. Liquid nitrogen-based freezers are organized differently, but again the ideas presented here also apply to those freezers, as well as freezers at other temperatures, FFPE storage systems, and so on.

Figure 2:
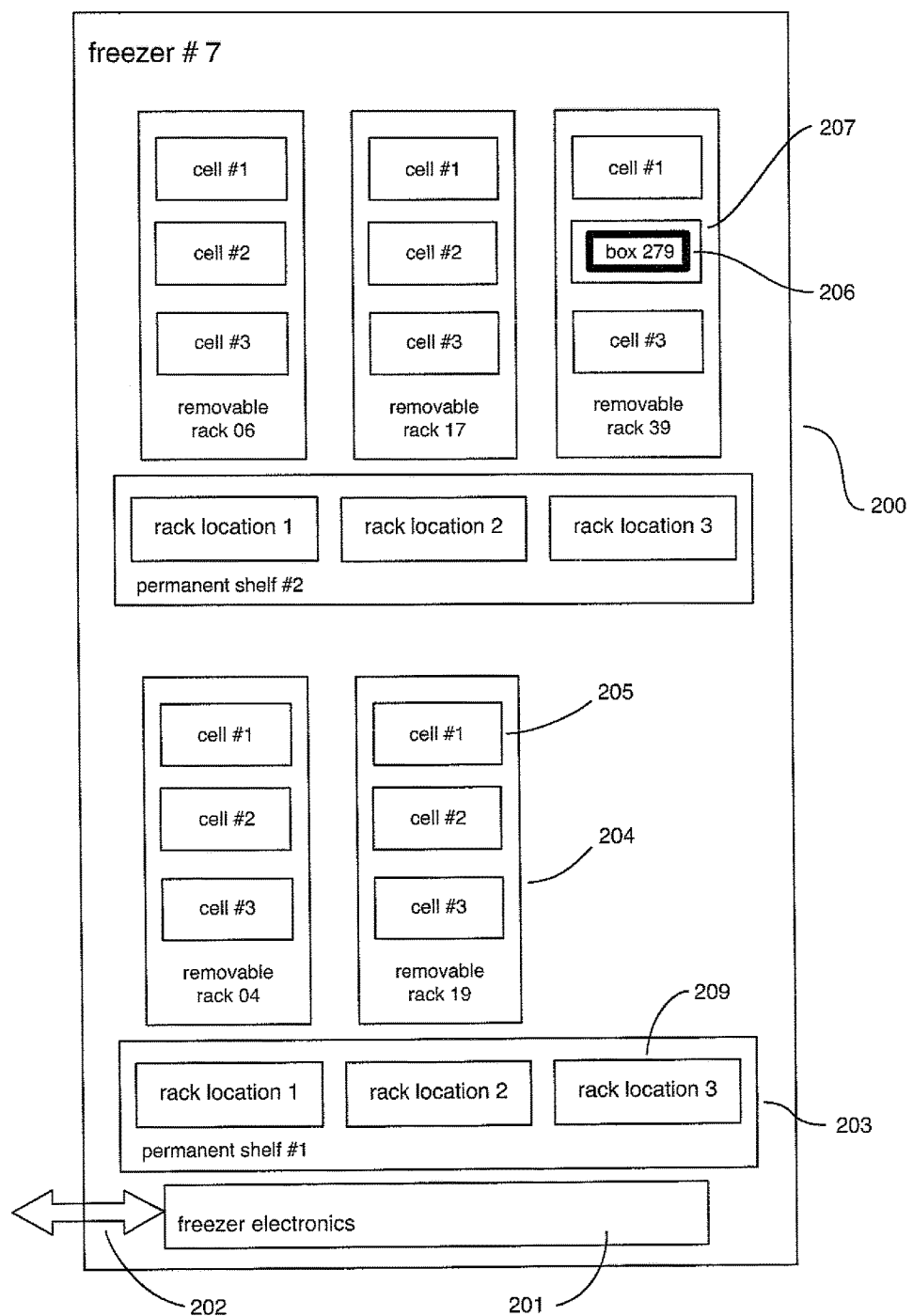
FIG. 2 shows a schematic view of an exemplary, simplified freezer storage system.

FIG. 2 shows a schematic view of an exemplary, simplified freezer storage system 200 having two shelves 203, each shelf having three rack locations 209 capable of receiving up to three racks 204, each rack having three cells 205 capable of receiving up to three boxes 206 of vials (not shown). Alternative embodiments can have different and differing numbers of shelves, rack locations, and/or cells. The freezer has built-in electronics 201 that can be completely internal to the freezer (as in the embodiment of FIG. 2), completely external to the freezer, or split into different subsystems, some of which are internal to the freezer and the rest external to the freezer. In FIG. 2, electronics board 201 is connected to the outside world via a bidirectional wireless or hardwired connection 202 such as USB, Ethernet, Bluetooth, optical, acoustic, or any combination thereof.

The freezer has semi-permanent shelves 203. By semi-permanent, we mean that the shelves can be reconfigured in a freezer, for example, by being moved up or down, removed, added, or swapped. But they will normally not be reconfigured in day-to-day use of the freezer.

Each shelf 203 has rack locations 209. A rack 204 can occupy any of these rack locations. The racks themselves can be moved within a freezer, removed from the system, or moved to another freezer. The shelves 203 may or may not be fully populated with racks. That is, a rack location may be left empty, such as rack location 3 on shelf #1 of FIG. 2.

Each rack 204, in turn, can hold one box 206 in each cell 205, where the cells may or may not be populated with boxes.

One goal of the system is to locate a specific box in the freezer without opening the freezer. This goal needs to be achieved even when racks and boxes can be removed, missing, moved from another location in the freezer, or added from another freezer altogether. As a concrete example, the location of the box 206 marked by the bold line in cell 207 would have an address of freezer 7, shelf 2, rack 3, box 2. So, if one would go to freezer #7 and look at the rack at location #3 on shelf #2 (this particular rack has a serial number of "39"), one would find a box with an ID number of "279".

We emphasize that label 206 denotes a particular item, box #279, while label 207 denotes a particular cell or box location (box position #2) that can be occupied by any box. The number of hierarchical layers in the system presented here is 4, where the layers are freezer, shelf, rack, and box. The number of layers can be different in alternative embodiments. For example, in a freezer where we are interested in tracking sample vials, a fifth layer can be added, which, in this case, would yield the following 5 layers: freezer, shelf, rack, box, and vial. In another example, if all we want to do is track racks (in the case where racks are sealed with unchanging contents, for example), the box layer could be removed and the remaining 3 layers would be freezer, shelf, and rack.

Figure 3:
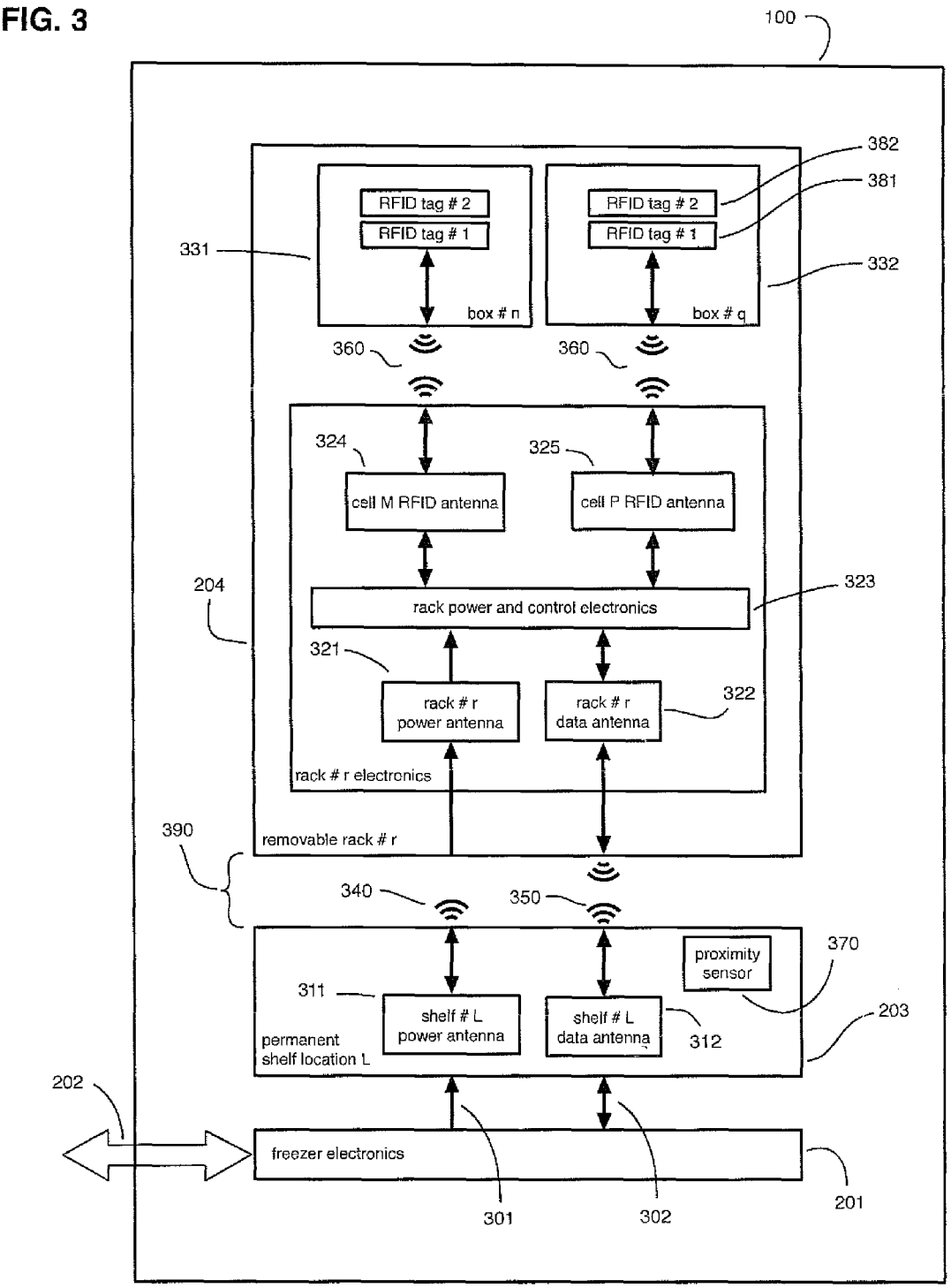
FIG. 3 shows a simplified, schematic block diagram of a portion of one shelf of the system of FIG. 2.

FIG. 3 shows a simplified, schematic block diagram of a portion of one shelf 203 of FIG. 2. In particular, FIG. 3 shows one rack 204 and 2 boxes 331 and 332. A typical freezer would contain more of each of these components as discussed above. Thus, the components in FIG. 3 will be repeated as many times as is necessary in a typical freezer. It will be obvious to one skilled in the art how a more-realistic system, with more components, could be built once the simple system shown in FIG. 3 is understood. We also note that a consistent hierarchy is not required. Indeed, any organization which routes to specific locations can be supported.

Again, we note that, where applicable in the ensuing discussion, we differentiate between a particular location and a particular item that occupies that location. Locations are designated with a capital letter, and the item that occupies that location is designated with a lower case letter. So, for example, in FIG. 3, shelf location L is occupied by rack r, and boxes n and q are located in cells M and P of rack r, respectively.

Internally, the electronics board 201 is connected to the electronics on the semi-permanent freezer shelf 203, typically one of many, via one or more wired connections 301, 302. At the very least, the freezer control board 201 distributes to each of the shelves via those wired connections a) one-way power 301 and b) two-way data signals 302. These connections can also be wireless, but, since the shelves are not moved in daily use, they can be physical, wired connections.

A shelf 203 can have a multiplicity of possible rack locations, only one of which, location L, is shown. At each location, the shelf electronics powers a so-called power antenna 311 mounted on the freezer shelf that provides power for the particular rack that is placed at location L, which, in this case, is removable rack r. Similarly, the shelf electronics also communicates data bi-directionally with removable rack r via a so-called data antenna 312. A physical gap 390 separates the rack from the freezer shelf. The gap distance may vary from zero to the maximum permitted by the performance of the electronics. The removability of the rack and the variable gap distance 390 preclude a wired connection between the rack and the shelf, but permits unidirectional and bidirectional wireless RF communication.

The antennae 321 and 322 in this particular rack r, which is likely one of many, are physically positioned to couple to antennae 311 and 312, respectively, which are located, in this case, at rack position L. This is done by positioning the rack 204 in relation to the shelf 203 in such a way that the antenna pairs 311/321 and 312/322 are strongly coupled. This can be achieved by using guide rails, sheet metal stops, bumpers, slots, magnets, or any other suitable mechanical means.

The antennae 321 and 322 are wired to, or are part of, the rack electronics board 323. This board controls the multiplexing of the data signals to the antennae at every possible sample box location or cell such as those designated M (324) and P (325). These antennae are positioned to couple to different removable boxes n and q in cells M and P, respectively. Communication between the boxes and the rack happens through wireless connections 360.

Each sample box 331, 332 contains at least one RFID tag 381 and possibly more RFID tags (a second RFID tag 382 is shown in FIG. 3). Here, too, suitable mechanical means are used to insure that box tags, such as RFID tags 381 and 382, are positioned correctly relative to the corresponding rack antenna 325.

How many RFID tags are in a box depends on the geometry of the read antennae 324, 325, the geometry of the box antennae 381, 382, the need to ascertain box orientation as described below and in PCT/US2012/32699, the teachings of which are incorporated herein by reference in their entirety and the redundancy required.

Power is delivered to the rack 204 through the wireless connection 340. This is a one-way RF path. The power antenna 311 that is attached to the freezer shelf 203 is located so that its power is received by antenna 321 on the removable rack 204. The RF signal from the receive antenna 321 is used to power the rack electronics board 323.

The wireless connection 350 is a bidirectional RF path used to communicate data and control commands between transceiver data antenna 312 located on the freezer shelf 203 and a corresponding transceiver antenna 322 on the rack 204. The data path is routed via the rack electronics 323 to multiple points within and external to the rack, including multiple, box RFID tag, transceiver antennae, such as antenna 325 used to communicate with RFID tags 381 and 382 attached to sample boxes via wireless connection 360.

Note that other arrangements between freezer and rack are possible. For example, both RF power and RF data could be conveyed via one antenna on each side of the physical gap 390, reducing the number of RF paths 340 and 350 to a single RF path. As another example, RF data and RF control over RF path 350 could instead be conveyed via different antenna pairs, increasing the number of RF paths to 3. Each RF path could use the same or different frequency than one or more of the other RF paths. Alternatively, the same path can be multiplexed such that multiple signals can be transferred at different frequencies or different times or any combination thereof.

The RF paths 340, 350, and 360 can be provided using any of a large variety of possible antenna types such as patch, slotted patch, dipole, monopole, Planar Inverted F Antenna (PIFA), single or multiple turn loops, and so on.

The proximity sensor 370 will be discussed in more detail below.

Figure 4:
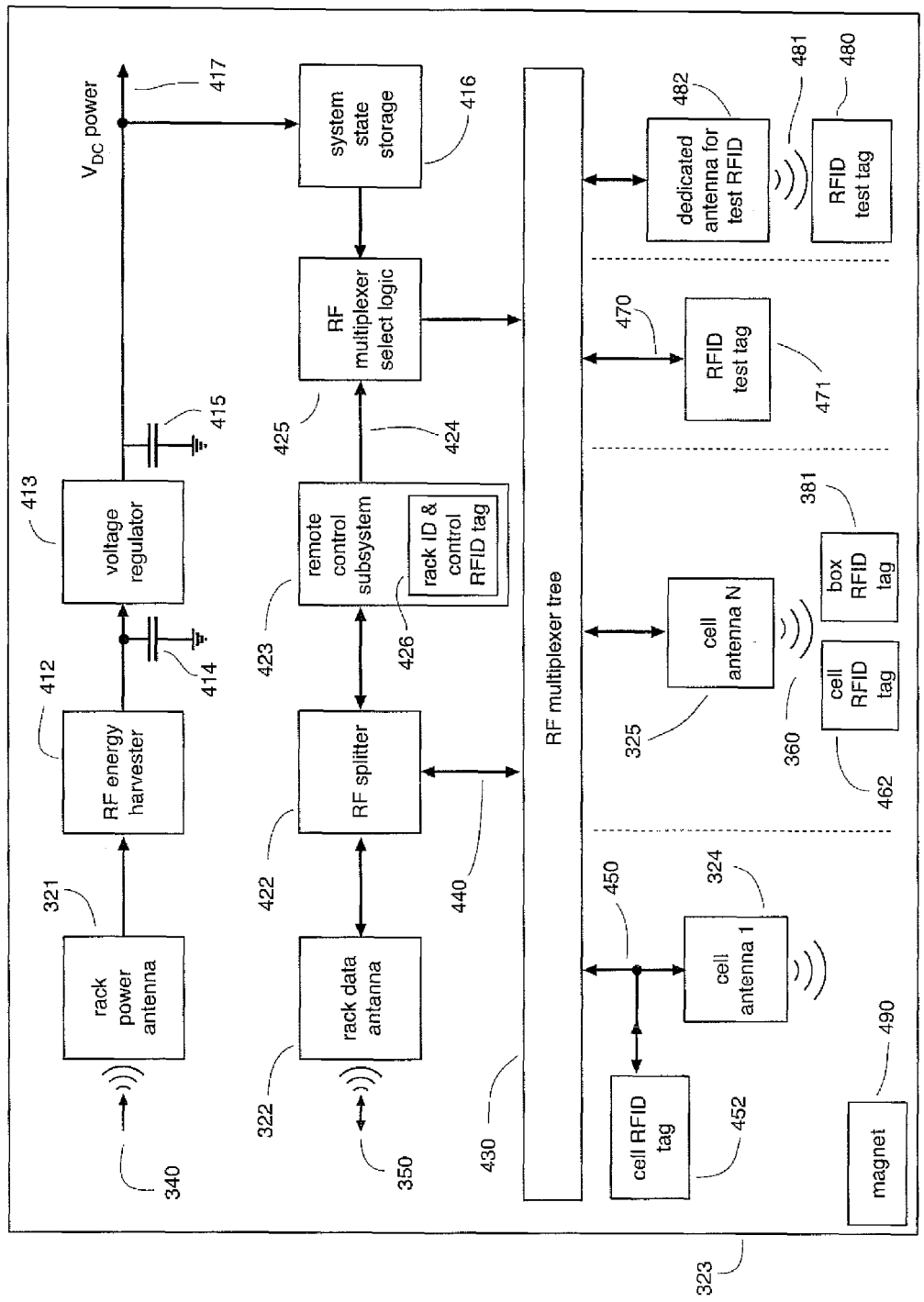
FIG. 4 shows a schematic block diagram of the rack electronics board of the removable rack of FIG. 3.

FIG. 4 shows a schematic block diagram of the rack electronics board 323 of removable rack 204 of FIG. 3. This board derives energy from RF power received via path 340 transmitted to the rack power antenna 321 from shelf power antenna 311 of FIG. 3 (not shown in FIG. 4).

The received RF power drives an RF energy harvesting subsystem 412, which supplies DC power 417 through voltage regulator 413 to the rest of the rack electronics board 323. This harvesting subsystem may require one or more external voltage regulators 413 as shown in FIG. 4. Alternatively, this voltage regulation function may be internal to the harvesting subsystem 412. The harvesting subsystem may have additional control inputs and status outputs (not shown). There may be more than one DC output voltage for operating the rack electronics, although only one output voltage 417 is shown in FIG. 4 to reduce the complexity of the schematics. Similarly, the power connections to the various subsystems on the electronics board are not shown.

The energy harvester 412 can be implemented using discrete components or might be implemented using dedicated parts such as a Powercast P2110 receiver from Powercast Corporation of Pittsburgh, Pa., or other, similar components.

The voltage regulator 413 can be supported by an input capacitor 414 and an output capacitor 415, if needed. The supply of RF power may be steady-state or intermittent. The combined, charge storage capacity of these capacitors are sufficient to support communication with one or more RFID tags, while maintaining a stable data path from the rack data antenna 322 to those RFID tags. Thus, in the case of intermittent RF power, the energy needed to power the electronics will be supplied by the capacitors 414 and 415. Alternatively, dedicated circuitry designed to maintain the system state storage 416 can be used as will be explained below and in FIG. 5.

The rack data antenna 322 receives and transmits bidirectional RFID data from and to shelf data antenna 312 and receives unidirectional control data from shelf data antenna 312 of FIG. 3 via RF path 350. In the embodiment shown here, a passive RF splitter 422 is used to deliver a minimal fraction of the incoming data path RF energy to the remote control subsystem 423, while the bulk of the incoming data path energy is routed via link 440 and a multiplexer tree 430 for distribution to the box RFID transceiver antennas such as antenna 324. How the incoming signal coming from antenna 322 is split in power and time by RF splitter A-B22 may vary from one embodiment to another. In a rack containing up to N cells, there would be N antennae of type 324.

One possible embodiment of remote control subsystem 423 may incorporate a passive or active rack identifier 426, which can serve to identify the rack or to control it or both. A rack identifier can serve various purposes, including:
 (1) Positively identifying the rack component using an RFID ID.

(2) Communicating with the rack regardless of the state of the power harvesting subsystem 412, since a passive RFID does its own energy harvesting from the data path.

(3) Maintaining information in the tag's programmable memory which can identify the rack geometry, its capabilities, history, etc.

(4) Reporting the information in item (3) above.

(5) Communicating status information back to the freezer electronics 201 of FIG. 3 via external I/O connections of the tag, including power subsystem and multiplexer tree states.

(6) Supporting encryption or security features to prevent unauthorized access to the rack.

The remote control subsystem 423 provides the appropriate signals 424 needed to select one branch of the multiplexer tree 430 using RF multiplexer select logic subsystem 425.

The RF multiplexer select logic subsystem 425 uses control outputs from the remote control subsystem 423 to select one path through the RF mux tree 430, connecting a branch of the RF splitter 422 (or independent antenna) to any one cell-to-box RFID transceiver antennae 324 or 461. Some multiplexer tree paths may be reserved for internal rack functions, for example, but not limited to, testing and diagnosis purposes.

There are several ways in which the multiplexer select logic 425 could be controlled. These might include:

(a) a free-running counter that would simply visit, in sequence, every possible multiplexer branch, (b) the detection of some predetermined RF carrier at a chosen energy and/or frequency, and (c) a RFID tag such as a rack identifier and/or control tag 426 or other circuit with one or more external outputs that could be used to transfer multiplexer control information in serial or parallel.

In case (c) tags such as the Monza X RFID tag by lmpinj, Inc. of Seattle, Wash., or an G2iL+ tag by NXP Semiconductors of Eindhoven, The Netherlands, or EM4325 from EM Microelectronics of Marin, Switzerland, can fulfill these purposes as well as the other functions described above. Minimally, one digital output from the RFID tag would be sufficient to control the multiplexer select logic.

In practice, the remote control subsystem 423 may produce a low-quality output 424, which should be conditioned before use with a comparator or level shifter, so that standard low-power digital logic may be used for the select logic subsystem 425.

In case (c) above (i.e., tag provided mux select code), much more control can be maintained since multiplexer tree branches can be repeated or skipped at will. Minimally, a single, digital output derived from the RF data signal 350 by the remote control subsystem 423 can advance the state of the select logic to select another mux tree path. For example, the digital output can clock an N-bit binary counter (not shown) to select among one of $2^N$ paths. If multiple outputs are available from the remote control subsystem 423, then these outputs could be used to shift a select state directly into a shift register (not shown). If many outputs are available, then the remote control subsystem 423 could directly output the mux tree select line states. In all cases, a system external to the freezer is expected to operate the remote control subsystem 423 via the freezer control electronics 201 of FIG. 3 and manipulate the available digital outputs to change the mux tree selection state. The internal freezer control electronics 201 could simply pass through commands received from outside the freezer via path 202, or respond to a high-level command and generate multiple low-level operations to the remote control subsystem 423.

We describe an efficient mechanism that provides feedback on the actual read state of the rack electronics system. In one embodiment, this is achieved using conventional RFID tags permanently incorporated into the rack electronics board 323. These internal RFID tags might be connected to the mux tree 430 in various ways, including:

(1) An wired connection to a rack-to-box RFID transceiver antenna path.

(2) A wireless coupling (radiative, inductive, or capacitive) to the electromagnetic field produced by a rack-to-box RFID transceiver antenna.

(3) A wired connection via an otherwise unused mux tree path.

(4) A wireless coupling (radiative, inductive, or capacitive) to the electromagnetic field produced by a transceiver antenna reserved for one or more internal tags.

While only one of the above cases would likely be used in any given embodiment, they are all shown together in FIG. 4 separated by dashed lines.

In Case (1), an wired connection 450 to a mux tree path associated with a cell-to-box transceiver antenna 324 is shown connecting a cell RFID tag 452. This connection, via a splitter (not shown), resistor divider (not shown), or other means, should minimally impair the power transfer to and from the cell-to-box RFID antenna 324 connected to the same path.

Case (2) uses an internal cell RFID tag 462 placed in the field 360 of a cell-to-box antenna 325. This arrangement relies on the existing, multiple access mechanisms of conventional tags to share the antenna 325 among multiple tags including, in this case, cell RFID tag 462 and tags mounted on a sample box such as 381 or 382 of FIG. 3 or both that are accessed via the antenna field 360.

Case (3) uses a dedicated mux tree path 470 to detect a dedicated test tag 471. Here there is less concern with distinction between cell and box tags. The connection to the tag is wired. Such a tag may also be used for testing and to verify that stable multiplexer paths can be achieved and does not reside in a real cell location but is nonetheless in the multiplexer path.

Case (4) is similar to Case (3) except the connection to the dedicated cell RFID test tag 480 is via an RF signal 481 carried by a dedicated antenna 482 for this tag. Here, too, there is less concern with distinction between cell and box tags since any box tag will be detected poorly or not at all by the dedicated cell antenna 482 since it is not coupled to any box tag. Here, too, such a tag may be used for testing and to verify that stable multiplexer paths can be achieved.

It should be noted that tags such as tags 452, 462, 471, and 480 serve a different purpose than the rack ID and control tag 426. The purpose of tag 426 is to identify the rack and perhaps to facilitate implementing instructions for reading the boxes. The purpose of tags 452, 462, 471, and 480 is to verify what box location, or cell, is being read. The RFID tag ID or selected subsets of the RFID data, such as the item reference number, can be used to distinguish between rack tags, cell tags, and box tags. Alternatively, the programmable tag memory can be used to distinguish cell tags from box tags. In one embodiment, this differentiation can be achieved using RFID data components as defined by the ISO 18000-6C or EPC Gen2 standards.

An alternative approach is to use tags that conform to the ISO 18000-6D standard. Here, tags can be preconfigured to emit the tag data multiple times at random delays after being powered up by the RF carrier. This is an alternative tag access method that relaxes the requirement that the tag be able to correctly decode messages from the reader. These tags can be used as box or cell tags in an autonomous switching design where the system wakes up in a random state and eventually visits all possible cell locations. Again, a series of reads in which a box tag is bracketed by the same cell tag can be presumed to be located in that cell. Tags that conform to ISO 18000-6D cannot be used as rack or switching apparatus control tags where it is necessary to receive instructions from the reader.

In Cases (1) and (2), once a certain box location has been successfully selected, two types of tags might be read: box tags and cell tags. A location-specific cell tag 452 or 462 will serve to notify the supervising system that the required box location has been selected successfully by the multiplexer tree. If no box is present, then no box tag will be detected. One or more box tags would indicate that a box has been detected. The number of box tags detected would depend on how the box has been tagged.

Using conventional RFID tags, either accessed via the mux tree, or incorporated into the remote control subsystem, the return signal strength indication (RSSI) built into the reader may be used to evaluate the freezer-to-rack coupling efficiency and determine if the rack is positioned properly for satisfactory data and power transfer. By timing the application of RF power to the RF energy harvesting subsystem, and testing via rack tag access when and if the internal tags can be reached, the state of the subsystem can be evaluated as will be described below.

An issue may arise when a rack is put in place but no communication is established with the rack. The system will incorrectly assume that the rack is simply not in the freezer. To prevent this situation, an independent rack proximity sensor 370 of FIG. 3 can be added to the shelf. Rack detection can take the form of a capacitive or inductive measurement that would detect the proximity of the rack using a change in capacitance or eddy current power absorption by rack metal. Alternatively, a magnetic field sensor such as the Honeywell HMC1501 Magnetic Displacement Sensor by Honeywell International, Inc., of Morristown, N.J., or equivalent, could detect the presence of a rack that contains a magnet 490 of FIG. 4. If it is found that a rack exists in a certain location but is not properly positioned, then the user can be alerted with an audible alarm, flashing icon, etc., so that he or she will position the rack properly. In one embodiment, the alert could appear externally to the freezer via a user interface device, display panel, etc. In another embodiment, the alert could appear internally to the freezer via an LED 105 of FIG. 1 on the freezer shelf.

The rack LEDs 104 and the shelf LEDs 105 of FIG. 1 can indicate to the user a variety of things using different blinking states or colors. As an example, in one embodiment, when the user places a rack in the system, an LED can blink showing that the rack has passed power-up testing and is properly communicating with the freezer. Color LEDs can be used as well. For example, green can be used if all of the rack subsystems are working properly and red if not. The LEDs can indicate a variety of things including, but not limited to, successful or unsuccessful control signal handshakes, correct or incorrect voltages, successful or unsuccessful rack ID reads, etc.

The LEDs need operate only when the freezer door is open. Where they would be located, e.g., on the freezer (105) or on the shelf (104), would be determined by the nature of the signals indicated. The rack LEDs 104 can also be used for guided retrieval of samples as discussed in U.S. patent application Ser. No. 13/026,359.

Using enhanced RFID tags (such as the Monza X and the G2iL+ mentioned above) with remotely accessible digital or analog inputs, subsystem status may be more directly monitored. For example, a tag with a single digital input can monitor the output of a comparator, and thus confirm that the DC output voltage 417 of the harvester subsystem 412 exceeds a set voltage threshold. A more-complicated arrangement could interact with an analog-to-digital converter (ADC) and make a high-resolution measurement of the voltage level. Similarly, the selection state that routes the RF to a particular location, in part or in total, could be monitored with such tag inputs.

When a box tag is read, processing is performed to confirm whether the multiplexer state was correct. This can be done in a variety of ways. The selection state, S, can be sent to the rack and read back to verify that it is correct along with other system information such as signals that would indicate a reset, low voltages, and other errors.

Alternatively, if every cell has its own tag, then the cell tag can be read, then a box tag can be read, and finally the cell tag can be read again to bracket the box tag by successful cell-tag reads that confirm that the multiplexer state is correct and has not changed.

With these feedback mechanisms from enhanced RFID tags, with or without external connections, it can be determined among other things that the RF multiplexer select state has reached at least one known state. For example, a rack tag located in the reading field of a single box antenna will confirm, when detectable within a predetermined RSSI range, that the corresponding mux tree selection state has been reached.

The mux tree selection state is needed to properly associate a box tag with the corresponding rack position where the box is located. Either (i) the selection state should be set with a highly reliable control method or (ii) the selection state should be determined with a highly reliable observation method, or both. If the remote control process permits directly setting the selection state, for example, by setting multiple control outputs from a new type of remotely controlled RFID tag, then there is no ambiguity. If the remote control process can only stimulate a stepwise change in selection state, then steps should reliably occur or the resulting state should be observed. The most-reliable observation method is to design the rack to provide an internal tag for every selection state for which reading a box tag is possible. Information about which box-location RFID tags are at which physical locations can reside in the remote control subsystem 423.

Another observation method is to provide confirmation of one or more selection states, but not all of the states. Such a design depends on the reliability of the selection-state control process, since transitions will occur between confirmed and unconfirmed states. Statistics for correctly reaching the observed states can be used to measure the reliability of the selection-state control process. If the control is highly reliable, then a design can be implemented which depends on (i) observing that a subset of selection states has been correctly reached and (ii) retrying the selection process when this occasionally does not happen.

For example, if the selection logic steps deterministically through a set of selection states, but the step stimulus is not reliable, then knowledge that a specific state has been reached will confirm that an expected number of steps occurred. If step stimuli may be both missed or unintentionally repeated, then returning to this specific state after the expected number of external stimulus commands does not insure that all intermediate states were reached once per external command. However, the process may be used to measure the statistical probability of either type of stimulus error. If only one type of error occurs, then the probability that wrong intermediate states might have occurred can be a guide to repeating the cycle until the known state is reached with the correct number of external commands.

For example, suppose the following statistics are measured for 10,000 trials:
(1) In 9,990 trials, known state reached after k=N commands, as expected.
(2) In 10 trials, known state reached after k=N+1 commands.
(3) In 0 trials, known state reached after k=N−1 commands.
(4) In 0 trials, known state reached after some other k commands.

It can be inferred that sometimes the stimulus command is missed, so extra commands are sometimes required. Also, extra stimuli do not seem to occur. Based on this, all of the box-tag locations can be expected to be reached correctly in one pass, for 99.9 percent of passes through all mux-tree states. In 0.1% of the passes, the cycle cannot be trusted and should be repeated, since box tags read during the cycle may be erroneously associated with the wrong tree state.

Even with the foregoing method, correct association of box tags with mux-tree states is not insured with certainty. The method relies on prior statistical measurements to reduce the probability of error to some possibly tolerable level. However, the statistics are not guaranteed to be constant for all freezers and all environments.

The box-tag-to-mux-state association can be confirmed with certainty only by placing an internal tag on every mux-tree path used to access box tags. Without issuing mux-tree state-change commands, 3 or more reads via the mux tree will confirm the tree state, as follows:
(1) Read until the internal tag is detected. If the wrong internal tag is detected, then exit.
(2) Read box tag(s) after reading the correct and only the correct internal tag, on the same read or a subsequent read.
(3) Read the correct and only the correct internal tag, after reading box tags, on the same read or a subsequent read.

With the correct internal tag detected before and after any box tags, with no other internal tag detected in the meanwhile, it can be concluded that the desired mux-tree state was reached and maintained while reading the intermediate box tags. Note that a particular multiple-tag access read pass may result in internal tags and box tags being read, but not in the desired order. Thus, other read passes would usually be required.

In summary, once a multiplexer state is set and box-tag reads are bracketed with correct cell-tag reads, we can be certain that the box was read at the correct multiplexer state.

Ultimately, the select logic 425 should provide stable and known select-line outputs for the duration of one RFID tag access session. This is typically tens of milliseconds, but depends on the RFID tag technology. In any case, each path to a box tag, or tags internal to the rack electronics, should be selectable with fairly uniform probability.

Figure 5:
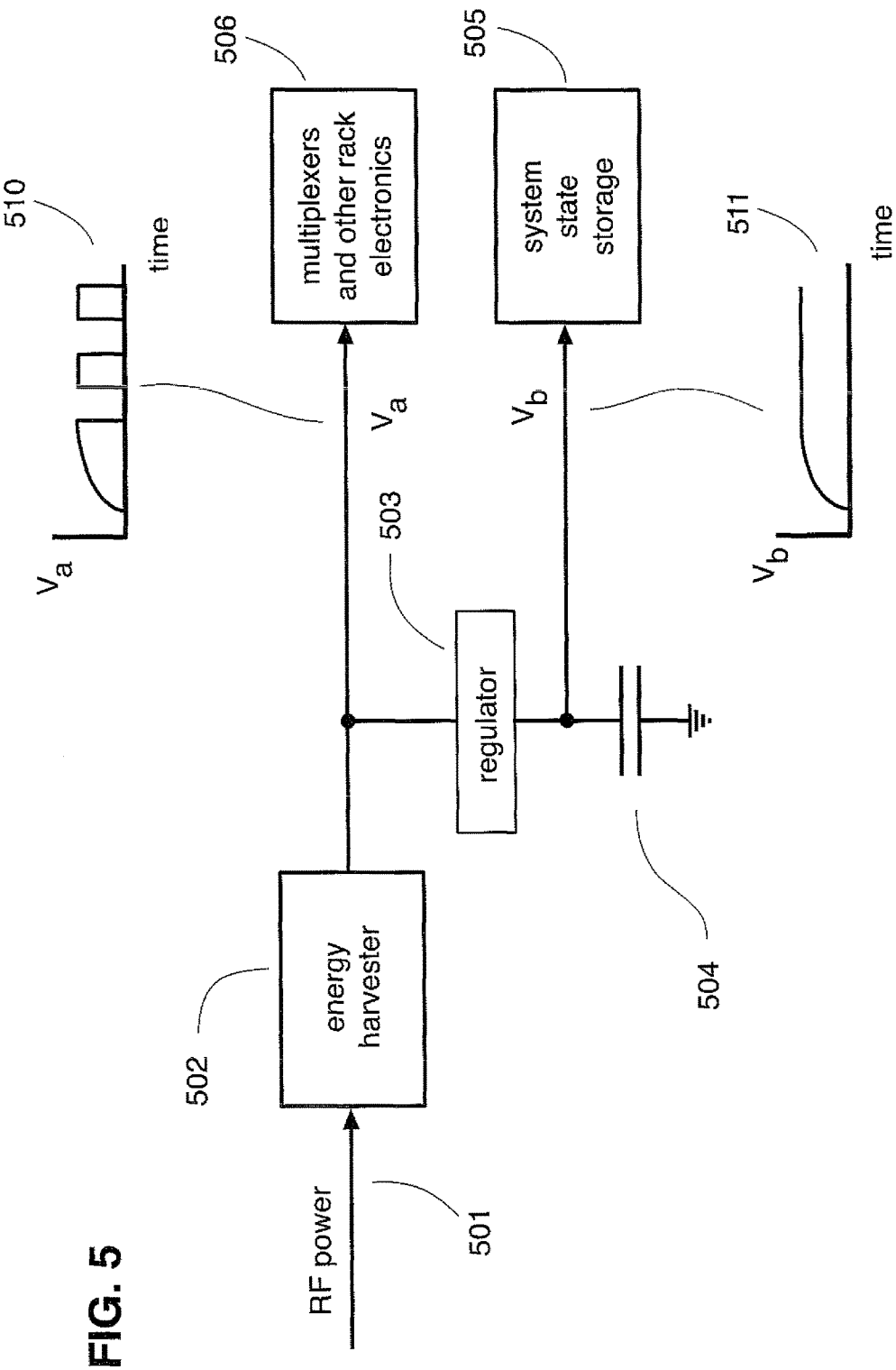
FIG. 5 shows a schematic block diagram illustrating the operations of a power harvester analogous to the power harvester of FIG. 4.

FIG. 5 shows a schematic block diagram illustrating the operations of a power harvester 502 analogous to power harvester 412 of FIG. 4. When using power harvester 502 to power the rack electronics, it might not be possible to supply enough RF power 501 in the 860 MHz-960 MHz RFID frequency band to continuously supply voltage to the RF multiplexers 506 and to maintain the multiplexer select state. In this case, the harvester output voltage $V_a$ will cycle as its power is depleted as illustrated in the plot 510 of $V_a$ vs. time.

If all components of the rack electronics are simultaneously powered, then the select state S will be lost when power is depleted. The system state storage 505 determines what the state of the multiplexer tree is at any given moment. In one embodiment, the system state storage might be a simple counter. In that case, when power is cycled, the counter will be reset and will have to cycle through its various states until a desired multiplexer is selected. This is time-consuming (several ms per count) and wastes the harvested power that has been accumulated.

A CMOS-based counter has a very low supply current requirement, significantly lower than that of typical UHF RF multiplexers. Thus, to resolve this issue, it is possible to isolate the voltage providing power to the counter 505 using a regulator (a diode might suffice here in some implementations) 503 and capacitor 504, which will maintain the voltage $V_b$ to the counter for at least hundreds of milliseconds, more than the time between output pulses of the harvester. This is illustrated in the plot 511 of $V_b$ vs. time. This way the counter will maintain its count between such pulses. Therefore, the extra time and energy to get the counter to the desired state S will not be required, since it won't be randomized or reset to zero due to a power interruption.

FIGS. 6(A) and 6(B) show simplified block diagrams of portions of an exemplary implementation of freezer system 100 of FIG. 1, while FIG. 6(C) shows a figurative view of a multi-component rack antenna 620 for system 100. In system 100, a single RF signal is used both to power the rack board and to read rack and box tags.

Referring to FIG. 6(A), an RF signal is generated by the RFID reader 601 that is located in the freezer electronics (e.g., 201 of FIG. 3). This signal is hardwired or multiplexed to all of the shelf antennae in the freezer. For simplicity, only one shelf antenna 603 is shown. In this embodiment, shelf antenna 603 combines the functions of antennae 311 and 312 of FIG. 3.

Only a few representative matching circuits 602 are shown in FIG. 6(A) to avoid cluttering the figure. In reality, matching circuits will be located anywhere impedance matching is needed in the RF path. Matching circuits can be active or passive, single- or multi-component, and might be used to achieve impedance matching between various components in the system. For example, an RFID reader chip typically has a 50-Ohm output, but, for reasons of circuit board design, it might be useful to have another impedance for the printed circuit board traces. The matching circuits can match those impedances with minimal loss, as needed.

The data and power signals are transmitted to the rack antenna 604, which combines the functions of antennae 321 and 322 of FIG. 3. The rack electronics 323 are shown in FIG. 6(A) bounded by the dotted line. The received signal 606 is sent to an RF splitter 607, which can be a combination of any number of components, such as directional couplers, circulators, coupled capacitors, coupled inductors, etc. The signal is fed into RF splitter 607 in such a way that the power used for energy harvesting 412 is sufficient to power all of the electronics on the rack board. Energy from the RF signal is converted by the energy harvester 412 to DC power after which it is conditioned, if necessary. The voltage 417 is distributed (not shown) to the rest of the board.

In addition, the RF signal is used to read the rack RFID and to control the multiplexer state control electronics 610, which represents components 423, 426, and 425 of FIG. 4.

It also passes to the multiplexer tree 611 and from there to the cell antenna and tags using one of the methods shown in FIG. 4. In most embodiments, the power supplied to the energy harvester will be larger than the power supplied to the multiplexers and control electronics.

Figure 6:
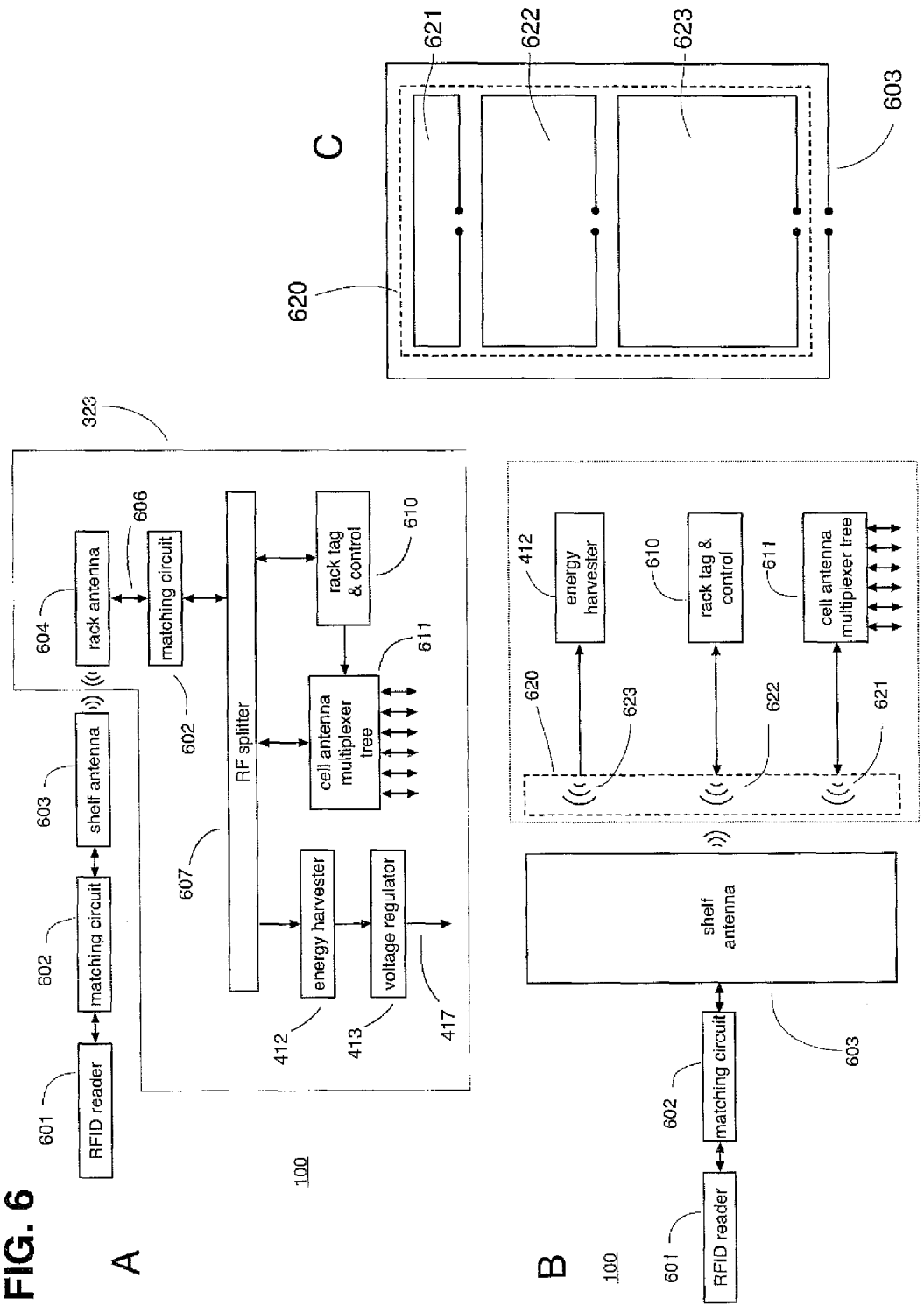

The circuitry of FIG. 6 serves the following purposes:
(1) Most of the RF power 606 is diverted to energy harvester 412 to generate power 417 for the rack electronics.
(2) Some of the RF energy is siphoned off to read the various rack, cell, and box RFID tags through mux tree 611 and control electronics 610.

FIG. 6(B) shows one possible embodiment of how the RF splitter 607 might be designed. Similar to FIG. 6(A), power and data are sent from the RFID reader 601 to the shelf antennae 603. This signal is coupled to multi-component rack antenna 620, shown enclosed in a dashed line, which has 3 component antennae 621, 622, and 623. Here, the radiated power from shelf antennae 603 is simultaneously received by all of the downstream components of the system including the energy harvester 412, the rack tag and control electronics 610, and the box and rack position tags via mux tree 611.

FIG. 6(C) shows an example of one possible embodiment of how power can be apportioned using simple antenna geometries. Here, all of the antennae 621, 622, 603, and 623 are simple, single-loop antennae, although they could be any of a large variety of possible antenna types such as patch, slotted patch, dipole, monopole, PIFA, single- or multiple-wind loops, and so on. Here, single-loop antennae are shown because they are readily understood due to their simple geometry. The exact same principles can be applied to the other antenna types mentioned above even if the geometric details will vary for each antenna type.

To divide the power between the different circuits, the antenna-coupling coefficients are selected based on the desired power ratios. The coupling coefficients will be dependent on the antenna areas, tuning, etc. If (i) most of the power is to go to the energy harvesting circuit 412, (ii) most of the remaining power is to go to the box and rack location tags, and (iii) the remainder is to go to the rack identifier tag with the power ratios of 8:5:2, then the coupling coefficients of the antennae 623, 622, and 621 are set to be 8:5:2, while covering all of the area of the power-feeding shelf antenna 603.

This scheme has the advantage that no components other than PCB traces are needed to implement it.

A disadvantage is that the ratios are set and symmetric so that, in the case of the above ratios, less than 2% of the rack identifier tag signal will be backscattered to the RFID reader.

Figure 7:
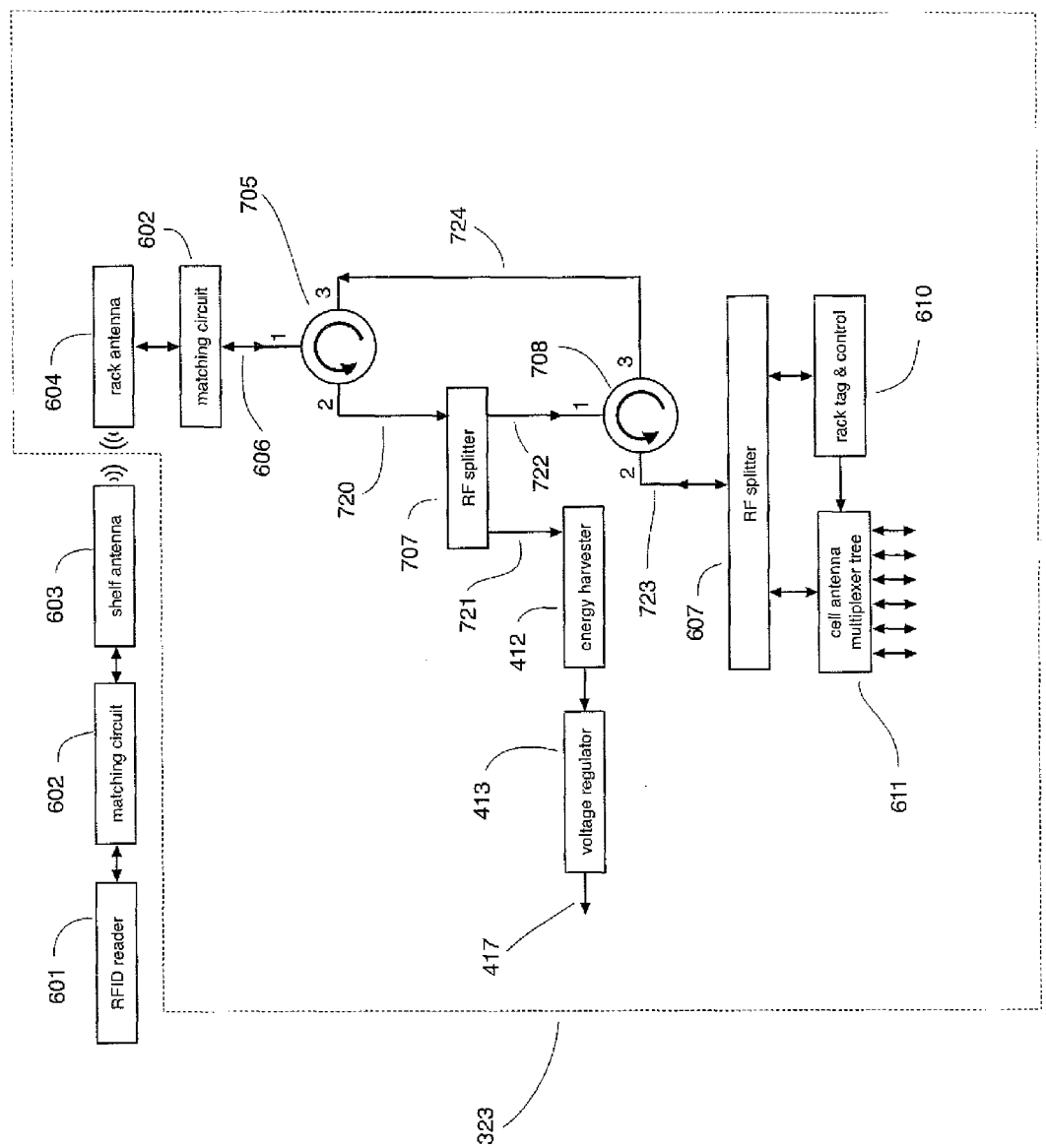
FIG. 7 shows a simplified block diagram of portions of another exemplary implementation of the freezer system of FIG. 1.

FIG. 7 shows a simplified block diagram of portions of another exemplary implementation of freezer system 100 of FIG. 1. This figure elaborates on some of the components shown schematically in FIGS. 2-4. As before, matching circuits can be incorporated wherever they might be needed but have been left out for the most part in the interest of reducing clutter in the figure.

First, an RF signal is generated by the RFID reader 601 that is located in the freezer electronics. This signal is hardwired or multiplexed to all of the shelf antennae in the freezer. For simplicity, only one shelf antenna 603 is shown, which combines the functions of antennae 311 and 312 of FIG. 3, as was previously discussed as a possible design option. Shelf antenna 603 transmits data and power to the rack antenna 604, which similarly combines the functions of antennae 321 and 322 of FIG. 3. The received signal 606 is sent through a circulator 705. The outbound signal 720 passes through the circulator 705 and is then fed into an RF splitter 707 in such a way that the power used for energy harvesting 412 is sufficient to power all of the electronics on the rack board 323. In most embodiments, the power 721 will be larger than the power 722. Energy from the RF signal 721 is converted to DC power by the energy harvesting circuit 412, after which it is conditioned, if necessary by voltage regulator 413 and distributed 417 to the rest of the board.

The RF power 722 is sent through another circulator 708 that sends the power to an RF splitter 607 that directs the power to rack tag and control unit 610, which represents components 423, 426, and 425 and the multiplexer tree 430 for reading slot tags (not shown) and/or box tags (not shown) using one of the methods shown in FIG. 4.

The circuit of FIG. 6 serves the following purposes:
1. Most of the RF power 606 is diverted to energy harvester 412 to generate power 417 for the rack electronics.
2. Some of the RF energy 722 is siphoned off to read the various rack, slot, and box RFID tags.
3. This energy is efficiently delivered via path 723 to the various rack, slot, and box RFID tags with minimal loss.
4. The backscattered signal 724 is coupled back efficiently to the RFID reader 601 with minimal loss for reading the RFID tag data.

The following discussion applies to both room-temperature box mappers and in-the-freezer vial-and box-tracking systems described in the patents and patent applications cited above. The goal is to read the box RFID tag regardless of the box orientation in the rack. Additionally, it is useful to know the orientation of the box to know where each sample is. This is especially important for desktop readers where samples need to be manipulated. We elaborate here on the strategies for tagging boxes and how to read them to achieve these goals.

Figure 8:
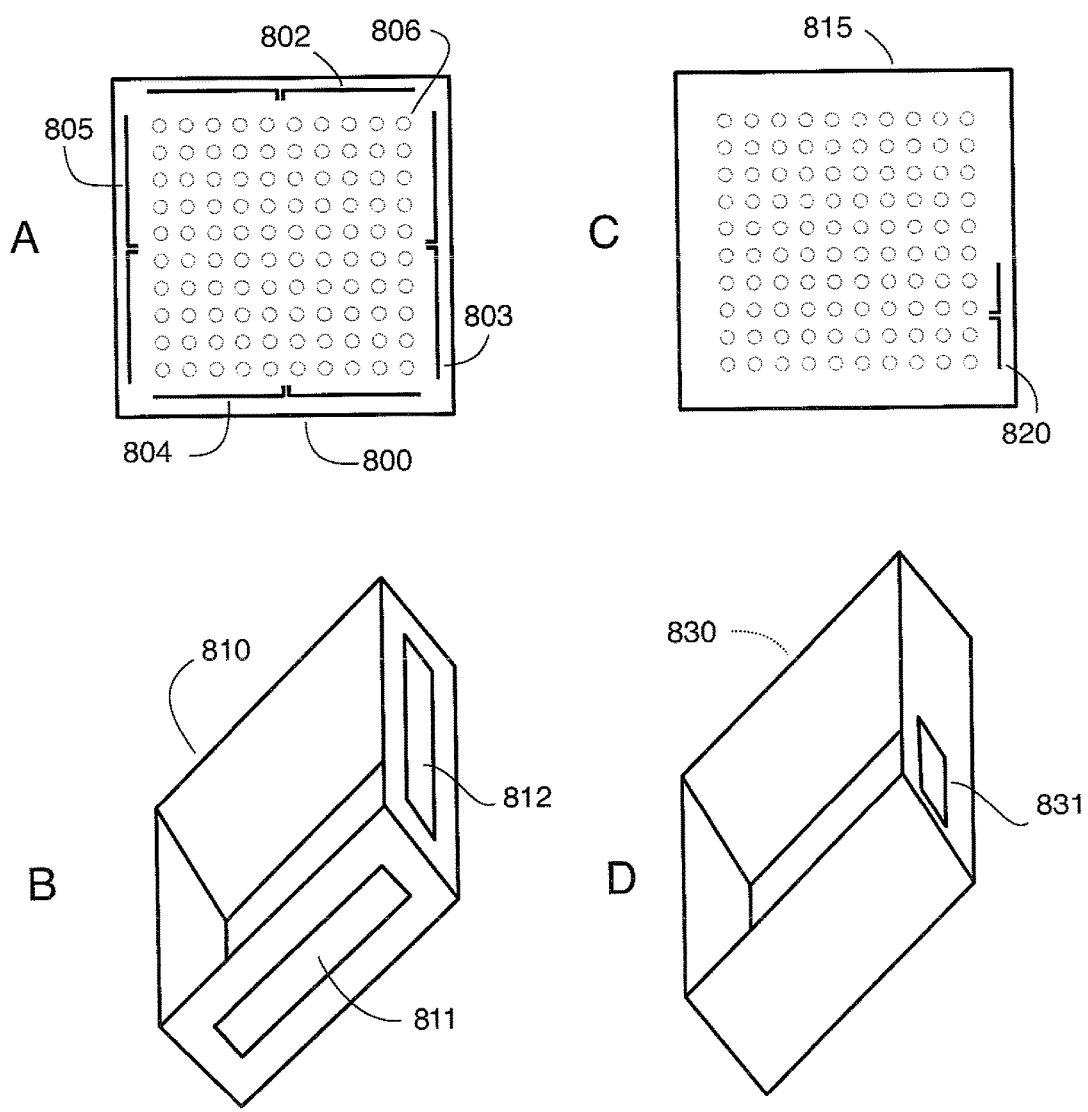
FIG. 8(A) shows a top view of an exemplary box read antennae board for a shelf cell that reads the RFID tags in vials contained in a box that is positioned on that shelf cell.
FIG. 8(B) shows a perspective view of an exemplary box having two box tag antennae placed in such a way so that each box tag antenna can be read by one of the four box read antennae of FIG. 8(A)
FIG. 8(C) shows a top view of an exemplary box read antenna board having a small box read antenna.
FIG. 8(D) shows a perspective view of an exemplary box having a small box tag.

FIG. 8(A) shows a top view of box read antennae board 800 that would be employed in each cell of a rack.

In U.S. Pat. Nos. 8,346,382 and 8,378,827 and U.S. patent application Ser. Nos. 13/026,359, 13/437,980, and 13/684,653, the teachings of all of which are incorporated herein by reference in their entirety. an implementation of this system that also includes reading vials is described. Here, the objective is to read the RFID tags in vials contained in a box that is positioned on that rack cell. Vials are read using some arrangement of antennae 806, one version of which is shown in the figure. In a system that reads only box tags and not vial tags, the antenna array 806 would not be incorporated into antenna board 800.

For the purpose of reading the box tags, four dedicated box read antennae 802-805 can be integrated into the four sides of PCB 800. The box read antennae are shown as simple dipoles but could be any of a large variety of possible antenna types such as patch, slotted patch, dipole, monopole, PIFA, single or multiple wind loops, among others.

FIG. 8(B) shows a perspective view of a box 810 having two box tag antennae 811 and 812 placed in such a way so that each box tag antenna can be read by one of the four box read antennae 802-805 of FIG. 8(A) when box 810 is positioned over board 800. Typically, it is desired that the read antenna 802 will read only the box tag of the nearest neighbor box directly above it or to the side. To achieve this, low transmit powers and low reader sensitivities can be used.

FIG. 8(C) shows a top view of a box read antenna board 815 having a box read antenna 820, and FIG. 8(D) shows a perspective view of a box 830 having a small box tag 831, that would be read by read antenna 820 when box 830 is placed over board 815 with an appropriate orientation.

The box tags can be one of any number of RFID tags offered by any vendors such as Smartrac N.V. of Amsterdam, The Netherlands, Alien Technology of Morgan Hill, Calif., Avery Dennison Inc. of Miamisburg, Ohio, and Partnered Print Solutions of Dacula, Ga. Any adhesive used to attach a tag to a box or vial should not fail in the ambient temperature of the freezer.

The bottom of the box can also be used for placing box tags but this could interfere with reading vial tags. In FIG. 8(A), box read antennae 802-805 are placed outside of the area of the vial antennae 806. Alternatively, box read antennae can be placed within the bounds of the vial antennae 806 so long as the box read antennae do interfere with the operation of the vial antenna, and vice versa.

If there is only one read antenna 802 on board 800 and only one box tag antenna 811 on box 810, then there will be three box orientations for which no box tag will be read. To allow the box tag to be read regardless of its orientation, up to three more reader antennae 803-805 can be included in board 800 or one or more box tags 812 can be included in box 810 or a combination of both, as will be explained below.

Regardless of where the box read antennae are placed on board 800, the multiplexer tree that activates the vial antennae 806 can also multiplex the box tag reader antennae 802-G05. While it is possible to have 4 read antennae 802-805, it is not necessary. This would depend on how box 810 is tagged. A user might place a square box in one of four possible orientations into a rack cell, or a rectangular box in one of two possible orientations. Each box orientation results in different geometric relationships between box tag(s) 811 and 812 and reader antenna(e) 802-805. At least one geometric relationship should permit wireless coupling between at least one box tag and one reader antenna to detect and identify the box. If multiple read antennae read a particular box tag, then the relative signal strength of these reads can be used to determine to which read antennae the box tag is closest.

Figure 9:
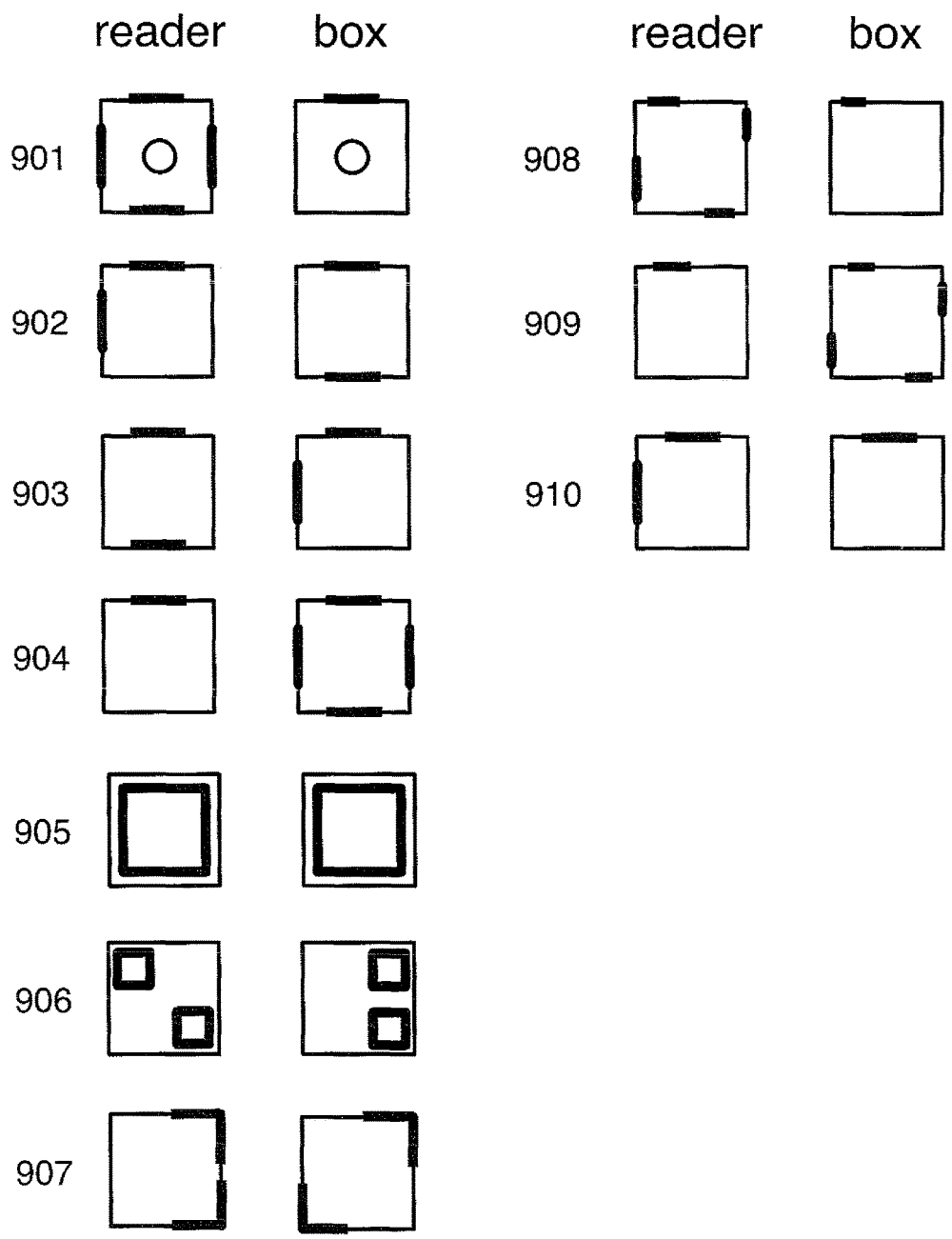
FIG. 9 shows top views of ten exemplary read antenna/box tag configurations.

FIG. 9 shows top views of ten exemplary read antenna/box tag configurations 901-910. In some of these configurations, the box orientation be known. In this figure, the box is shown offset to the right for clarity even though in reality, when a box is read, it will be placed on top of the reader. That is, the circular fiducial marks in H01 will be concentric. On the readers, the read antennae are shown in bold. On the boxes, the RFID tags are shown in bold. Thus, the tag configuration of box 810 of FIG. 8(B) is equivalent to that of the box in configuration 903, and the reader configuration of PCB 800 of FIG. 8(A) is equivalent to that of the reader in configuration 901.

Assuming that the orientation of the sample box is important to know, configurations 901 through 904 in FIG. 9 will always allow a box to be read and its orientation known.

At one extreme is configuration 901 which has 4 reader antennae. This complicates the reader design because more antennae need to be multiplexed, but it simplifies the sample box since only one tag is needed. At the other extreme is configuration 904 where the situation is reversed, and there is only one reader antenna and four box antennae. This design might be useful if read speed and reader simplicity are paramount.

If box orientation is not important, as might be the case in certain in-the-freezer designs, configuration 905 can be used. Here, the reader antenna is in the shape of a simple loop with a similarly shaped box tag antenna. However, here, the box orientation cannot be determined. The loops can be a small part of the box size or they can be as large as the box itself. A modification of this would be configuration 906 where the antennae are still simple loops but the orientation can be determined.

Other embodiments are also possible. In configuration 907, a corner reader dipole antenna is used to read corner wrapped dipole box tags. This ensures that at least one arm of the dipole and reader antenna are parallel, no matter the box orientation. As before, the reader and box tag orientations can be reversed similar to configurations 902 and 903.

Embodiments with smaller antennae are shown in configurations 908 and 909.

Other strategies can be used as well. For example, in configuration 910, the polarization of the dipole radiation would prevent the single box tag from being read by an orthogonal reader antenna. That understanding, coupled with a signal strength measurement, can be used to determine if the box tag is close to or on the other side of the box compared to the read antenna that is parallel to the tag.

An issue might arise when a particular read antenna reads more than one box tag, perhaps from two different boxes in adjacent rack locations. To disambiguate these instances, the RFID tags that are attached to a particular box can be paired in such a way that each RFID tag can supply information as to the ID of the other tag(s) that are attached to that same box. This can reduce the computational burden needed to determine the rack organization when multiple tags are read by each of the many rack antennae.

One method that can be used to solve this issue is the following: The TID (Tag IDentifier—a unique number that is different for every tag) or an unambiguous part of it can stored in the memory of the other tags attached to the same box. So, for example, if a box has two tags A and B, the tag can be programmed in the following way:

| Tag | TID | tag memory |
| --- | --- | --- |
| A | 777788889999 | 111222333444 |
| B | 111222333444 | 777788889999 |

This data might be incorporated in an extended EPC or in the tag memory such as that of the Monza 4 tag made by Impinj, Inc., of Seattle, Wash. Knowledge of these pairings can help parse out the location of the boxes in a rack when each of the many reader antennae read multiple tags from multiple boxes.

In another embodiment, the box tags could be chosen based on some criteria, without programming them, where they would be placed in a box. The EPC and TID values are fairly uniformly distributed, certainly for bits in the LSB end of the range. Here, it can be decided, for example, that, in the case of 4 box tags as shown in configuration 904, 2 bits determine where a tag will be located so that for these 2 particular bits K, K={0,0} for upper left corner
K={0,1} for upper right
K={1,0} for lower left
K={1,1} for lower right.

This is easy to check, and no programming is required. The user can even be provided a spare tag kit of 4 tags and guide the customer to select and replace the correct broken one if need be.

We can use this tagging scheme to read box rotation and to distinguish one box from another, if two box tags respond to the same read antenna. If we read a box tag using a read antenna that is placed at the upper right corner of a cell that is known to have been placed in the lower left corner of a box, we can conclude that this tag is on a nearest neighboring box and not a box in the cell.

In another embodiment, some other small range of bits could be constrained by selection of tags to match for one particular box. Finally, some other part of the tag chip memory space could be pre-programmed for a similar purpose. We also note that, for some purposes, global uniqueness is not required, just local uniqueness.

The same tag selection method just described for box tags, could be used to pick tree tags and be used to confirm a particular selection of a branch of a multiplexor tree. Say, in a given multiplexer path, for all racks, we place only chips with a certain value, say 14, in a certain range of their bit space. We can then determine that that particular path has been chosen if the ID that is read has 14 in that same bit space. This can be determined without accessing any database. However, the downside is that tags will be need to be carefully picked when assembling the racks.

We note the following for any and all of the above discussions:
1. Metallic shielding in the rack can be used to prevent coupling between reader antennae and tags on boxes that are located in a different rack location than the one being read.
2. Any suitable frequency range of RFID signals, such as LF, HF, UHF, or microwave, could be used.
3. For supplying power, the driving signal can be of any frequency and is not limited to RFID-dedicated frequency ranges.
4. Relative tag signal strengths can be used to remove ambiguity in the location of tags in the system. If two identical tags A and B, with the same orientation relative to a read antenna are read with signal strength 10 and 1, respectively, this information can be used to determine that tag A is closer to the read antenna than tag B. This kind of determination is usually not used in RFID systems, but can be useful here where the physical location of the tags is our primary concern.
5. In all of the box/reader configurations, more box tags than are necessary can be used for redundancy, which will greatly reduce the possibility of not being able to identify a box at all in case any one box tag fails.
6. More vial tags can be used as well in vials to reduce the possibility of encountering a vial with an unreadable tag. If a tag fails at a rate of 10e-4, then, assuming the failure is random, the chance of having two failed tags would be 10e-8.
7. Multiple energy harvesters can be used in various places, farther down the multiplexer path, if needed. For example, if vials will also be read, then the vial-reading antenna board needs to be powered as well, and it may be better to harvest the energy at the box level and not the rack level.
8. All of the above ideas are relevant to any storage system where part of the system is static, but with removable units that contain movable inventory. Let's take an example of catheters stored in bins in a medical cabinet in a hospital. The problem is that the staff needs to locate a certain catheter type quickly. The medical cabinet is considered stable (equivalent to the freezer in the discussion above), but bins (racks) containing catheters, can be removed, moved, switched, etc. The catheters (boxes) can be placed in the bins in any location. The system described above will enable staff to locate a certain catheter quickly in any size storage system.

We note that racks come in various shapes and sizes. While a table of how to arrive at a certain box location, L, in any given rack can reside in the host electronics, it is more efficient to store that data on the rack itself. The reason for this is twofold: a) this organization will never change once a rack is built and b) it also eliminates the need of building and maintaining a rack data base.

As was described above, a tag is built into the rack at every possible box location never changes. It serves to verify that the correct multiplexer tree state is correct as described above. This rack tag could be any one of tags 610, 451, 462, 470, or 480 described above.

Figure 10:
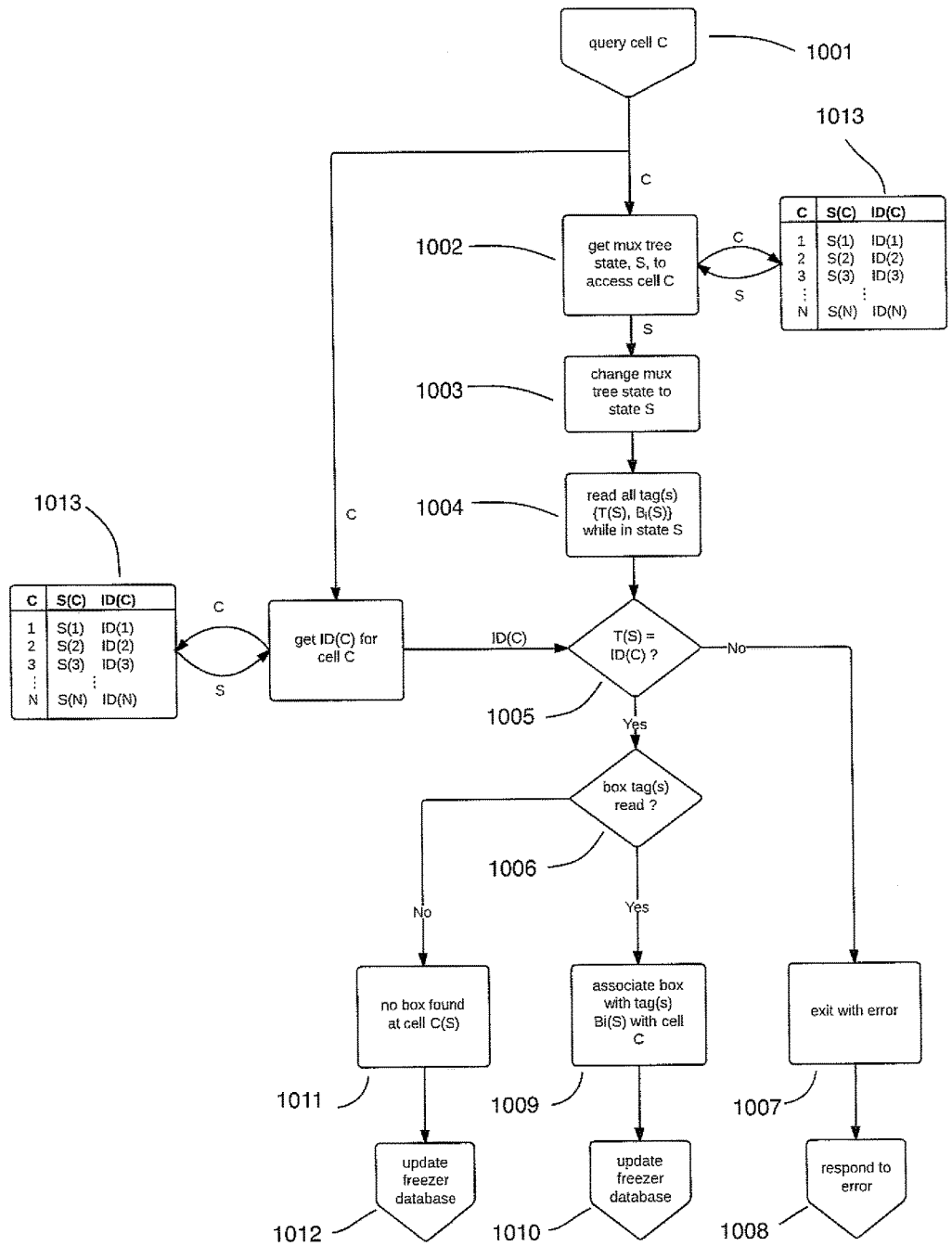
FIG. 10 shows a flow diagram of processing performed according to some embodiments of this disclosure by which a box location, L, is queried.

FIG. 10 shows a flow diagram of processing performed according to some embodiments of this disclosure by which a box location, L, is queried. The purpose of the query is to determine if a box is located in cell C and, if so, what is its RFID identifier, ID(C).

The query 1001 is made by the freezer electronics 201 in response to a general inventory request (in which the whole rack is read one location at a time) or as a request concerning the specific location C.

At step 1002, small table 1013 is accessed. It contains the following information for every possible rack cell C: a) the multiplexer state S(C) that will direct the RF signal to that location and b) the rack tag ID, ID(C) for that cell. This table can be located in a database in the host computer, the freezer electronics 201, or in the rack itself and uploaded to the freezer electronics. The system then executes a state change 1003 in the multiplexer-tree state to state S(C), which directs RF energy to the antenna at location C. At step 1004, all of the tags that are accessible in this mux-tree state are read. In general, this will include a cell tag with ID T(S) and one or more box tags $B_i(L)$ depending on which configuration of FIG. 9 and what level of box-tag redundancy are implemented in the design. At step 1005, the ID T(S) of the tag that was read is tested against the known value ID(C) stored in table 1002. If the IDs match, then we are very sure that the multiplexer state that was executed was the correct one. If not, an error 1007 is reported and processing proceeds to step 1008 where another attempt can be made or some other response can be taken. If the test at step 1006 shows that the mux path was set up correctly, any box tags that were read are associated with the cell C at step 1009, and the database is updated to reflect this information at step 1010. If no box tag(s) were read at cell C (1011), then the location is assumed to be empty and the database is updated accordingly at step 1012.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

The functions of the various elements shown in the figures, including any functional blocks labeled as "processors," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

It should be appreciated by those of ordinary skill in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Digital information can be transmitted over virtually any channel. Transmission applications or media include, but are not limited to, coaxial cable, twisted pair conductors, optical fiber, radio frequency channels, wired or wireless local area networks, digital subscriber line technologies, wireless cellular, Ethernet over any medium such as copper or optical fiber, cable channels such as cable television, and Earth-satellite communications.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A system for storing samples, the system comprising:
   a cabinet having a plurality of container locations, each container location configured to receive a container configured to store one or more samples, wherein:
      each container is configured with a container RFID tag; and
      each container location is configured with a different location RFID tag; and
   system electronics configured to support reading (i) each location RFID tag to enable the system to determine whether the system electronics is operating properly and (ii) each container RFID tag to identify the container location of each container stored in the cabinet, wherein the system is configured to determine that the system electronics are operating improperly by using the system electronics to attempt to read a known location RFID tag having a known RFID number at a specific container location, such that, if the actually read RFID number of the read location RFID tag does not match the known RFID number of the known location RFID tag, then the system determines that the system electronics are not operating properly.

2. The system of claim 1, wherein the system electronics is configured to:
   (a) read the location RFID tag at a corresponding container location to determine a location ID value of the location RFID tag;
   (b) compare the location ID value of the location RFID tag with a stored ID value for the corresponding container location in a database to verify that the read ID value matches the stored ID value;
   (c) read the container RFID tag to determine a container ID value of the container RFID tag; and
   (d) store the container ID value for the corresponding container location in the database.

3. The system of claim 1, wherein:
   the system electronics comprises cabinet electronics and multiple sets of shelf electronics;
   the cabinet is configured to receive a plurality of shelves, each shelf having a plurality of the container locations; and
   each shelf having a set of shelf electronics configured to support reading each location RFID tag corresponding to the shelf and each container RFID tag of each container stored on the shelf to enable the system electronics to identify the container location of each container stored on the shelf.

4. The system of claim 3, wherein the cabinet electronics is configured to transmit power to and communicate with each set of shelf electronics.

5. The system of claim 3, wherein:
   the system electronics further comprises multiple sets of rack electronics;

each shelf is configured to receive a plurality of racks, each rack having a plurality of the container locations; and each rack having a set of rack electronics configured to support reading each location RFID tag corresponding to the rack and each container RFID tag of each container stored on the rack to enable the system electronics to identify the container location of each container stored on the rack.

6. The system of claim 5, wherein, for each rack location on each shelf, the shelf comprises a rack indicator configured to indicate whether or not a rack is properly configured at the rack location.

7. The system of claim 5, wherein each set of shelf electronics is configured to wirelessly transmit power to and wirelessly communicate with each corresponding set of rack electronics.

8. The system of claim 7, wherein each corresponding set of rack electronics comprises circuitry for harvesting and regulating the power received from the shelf electronics.

9. The system of claim 7, wherein:
the set of shelf electronics comprises, for each rack, a shelf power antenna and a shelf data antenna;
each corresponding set of rack electronics comprises a corresponding rack power antenna and a corresponding rack data antenna;
the shelf power antenna is configured to transmit power to the corresponding rack power antenna; and
the shelf data antenna is configured to communicate with the corresponding rack data antenna.

10. The system of claim 9, wherein some of the power received by the corresponding rack power antenna from the shelf power antenna is used to power the corresponding rack data antenna.

11. The system of claim 7, wherein:
the set of shelf electronics comprises, for each rack, a single shelf antenna;
each corresponding set of rack electronics comprises a single rack antenna;
the shelf antenna is configured to transmit power to and communicate with the corresponding rack antenna; and
the corresponding set of rack electronics comprises circuitry configured to process (i) power signals and control signals received at the rack antenna and (ii) RFID data signals such that (1) the power signals and the control signals are split apart from a signal received at the rack antenna from the shelf antenna and (2) the RFID data signals are forwarded to the rack antenna for transmission to the shelf antenna.

12. The system of claim 7, wherein:
the set of shelf electronics comprises, for each rack, a single shelf antenna;
each corresponding set of rack electronics comprises a rack data antenna, a rack control antenna and a rack power antenna; and
the shelf antenna is configured to communicate data with the rack data antenna, communicate control with the rack control antenna, and transmit power to the rack power antenna.

13. The system of claim 7, wherein the corresponding set of rack electronics comprises:
one or more multiplexers configured to transmit and receive signals to and from selected container locations on the rack based on multiplexer settings; and
circuitry for storing a system state corresponding to the multiplexer settings of the one or more multiplexers to enable the corresponding set of rack electronics to recover from power cycling.

14. The system of claim 1, wherein, at each container location, the cabinet comprises a location antenna configured to wirelessly read the container RFID tag of a container stored in the container location.

15. The system of claim 14, wherein the location antenna is further configured to wirelessly read the location RFID tag of the container location.

16. The system of claim 14, wherein the location RFID tag of the container location is hardwired to the system electronics such that the location antenna is not required to read the location RFID tag of the container location.

17. The system of claim 1, wherein the cabinet further comprises a test RFID tag, wherein the system electronics is configured to read the test RFID tag in order to confirm proper operations of the system electronics.

18. The system of claim 1, wherein the system electronics comprise:
one or more power antennas configured to wirelessly transmit power towards the container locations; and
one or more data antennas configured to wirelessly transmit and receive outgoing and incoming communication signals towards and away from the container locations.

19. The system of claim 18, wherein:
the cabinet comprises a plurality of shelves, each shelf having one or more corresponding container locations; and
each shelf has at least one shelf power antenna configured to wirelessly transmit power towards the one or more corresponding container locations and at least one shelf data antenna configured to wirelessly transmit and receive outgoing and incoming communications signals towards and away from the one or more corresponding container locations.

20. The system of claim 19, wherein:
each shelf is configured to receive one or more racks, each rack having one or more corresponding container locations; and
each rack has at least one rack power antenna configured to wirelessly receive power transmitted towards the one or more corresponding container locations and at least one rack data antenna configured to wirelessly transmit and receive outgoing and incoming communications signals towards and away from the one or more corresponding container locations.

21. The system of claim 1, wherein the system electronics are configured to determine rotational orientation of a container at a container location.

22. The system of claim 21, wherein:
the container comprises one or more container RFID tags; and
the container location comprises one or more reader antennae configured to read one of the one or more container RFID tags, such that the system electronics are configured to determine the rotational orientation of the container at the container location based on results of the one or more reader antennae attempting to read the one or more container RFID tags.

23. The system of claim 22, wherein:
the container comprises two or more container RFID tags; and
the two or more container RFID tags and the one or more reader antennae provide redundancy such that the system electronics are configured to determine the rotational orientation of the container at the container location based on the results of the one or more reader antennae attempting to read the two or more container RFID tags, even if one of the container RFID tags fails.

24. The system of claim 22, wherein:
at least one container RFID tag wraps around a corner of the container; and
at least one reader antennae wraps around a corner of the container location.

25. The system of claim 1, wherein:
the container comprises two or more container RFID tags;
the system electronics are configured to establish a logical grouping of the two or more container RFID tags for the container; and
the system electronics are configured to use the logical grouping to determine when one of the reader antennae of the container location reads a container RFID tag of another container at another container location.

26. The system of claim 1, wherein:
the cabinet is a freezer for storing biological samples;
each container is a box of one or more samples; and
each container location is a box cell.

27. The system of claim 1, wherein the system is configured to identify a container at the specific container location by:
(1) using the system electronics to actually read the location RFID tag at the specific location;
(2) then using the system electronics to actually read the container RFID tag at the specific location; and
(3) then using the system electronics to actually re-read the location RFID tag at the specific location, wherein:
if the actually read RFID number of the read location RFID tag and the actually re-read RFID number of the re-read location RFID tag both match the known RFID number of the known location RFID tag, then the system determines that the read RFID number of the read container RFID tag is correct; and
if either the actually read RFID number of the read location RFID tag or the actually re-read RFID number of the re-read location RFID tag fails to match the known RFID number of the known location RFID tag, then the system determines that the actually read RFID number of the read container RFID tag is not correct.

28. A system for storing samples, the system comprising:
a cabinet having a plurality of container locations, each container location configured to receive a container configured to store one or more samples, wherein:
each container is configured with a container RFID tag; and
each container location is configured with a location RFID tag; and
system electronics configured to support reading each location RFID tag and each container RFID tag to identify the container location of each container stored in the cabinet, wherein:
the system electronics comprises cabinet electronics and multiple sets of shelf electronics;
the cabinet is configured to receive a plurality of shelves, each shelf having a plurality of the container locations;
each shelf having a set of shelf electronics configured to support reading each location RFID tag corresponding to the shelf and each container RFID tag of each container stored on the shelf to enable the system electronics to identify the container location of each container stored on the shelf;
the system electronics further comprises multiple sets of rack electronics;
each shelf is configured to receive a plurality of racks, each rack having a plurality of the container locations;
each rack having a set of rack electronics configured to support reading each location RFID tag corresponding to the rack and each container RFID tag of each container stored on the rack to enable the system electronics to identify the container location of each container stored on the rack;
each set of shelf electronics is configured to wirelessly transmit power to and wirelessly communicate with each corresponding set of rack electronics;
the set of shelf electronics comprises, for each rack, a single shelf antenna;
each corresponding set of rack electronics comprises a single rack antenna;
the shelf antenna is configured to transmit power to and communicate with the corresponding rack antenna; and
the corresponding set of rack electronics comprises circuitry configured to process (i) power signals and control signals received at the rack antenna and (ii) RFID data signals from the container and location RFID tags such that (1) the power signals and the control signals are split apart from a signal received at the rack antenna from the shelf antenna and (2) the RFID data signals are forwarded to the rack antenna for transmission to the shelf antenna.

29. A system for storing samples, the system comprising:
a cabinet having a plurality of container locations, each container location configured to receive a container configured to store one or more samples, wherein:
each container is configured with a container RFID tag; and
each container location is configured with a location RFID tag; and
system electronics configured to support reading each location RFID tag and each container RFID tag to identify the container location of each container stored in the cabinet, wherein:
the system electronics comprises cabinet electronics and multiple sets of shelf electronics;
the cabinet is configured to receive a plurality of shelves, each shelf having a plurality of the container locations;
each shelf having a set of shelf electronics configured to support reading each location RFID tag corresponding to the shelf and each container RFID tag of each container stored on the shelf to enable the system electronics to identify the container location of each container stored on the shelf;
the system electronics further comprises multiple sets of rack electronics;
each shelf is configured to receive a plurality of racks, each rack having a plurality of the container locations;
each rack having a set of rack electronics configured to support reading each location RFID tag corresponding to the rack and each container RFID tag of each container stored on the rack to enable the system electronics to identify the container location of each container stored on the rack;
each set of shelf electronics is configured to wirelessly transmit power to and wirelessly communicate with each corresponding set of rack electronics;
the corresponding set of rack electronics comprises:

one or more multiplexers configured to transmit and receive signals to and from selected container locations on the rack based on multiplexer settings; and circuitry for storing a system state corresponding to the multiplexer settings of the one or more multiplexers to enable the corresponding set of rack electronics to recover from power cycling.

30. A system for storing samples, the system comprising:

a cabinet having a plurality of container locations, each container location configured to receive a container configured to store one or more samples, wherein:

each container is configured with a container RFID tag; and each container location is configured with a location RFID tag; and system electronics configured to support reading (i) each location RFID tag to enable the system to determine whether the system electronics is operating properly and (ii) each container RFID tag to identify the container location of each container stored in the cabinet, wherein:

the system electronics are configured to determine rotational orientation of a container at a container location;

the container comprises one or more container RFID tags; and the container location comprises one or more reader antennae configured to read one of the one or more container RFID tags, such that the system electronics are configured to determine the rotational orientation of the container at the container location based on results of the one or more reader antennae attempting to read the one or more container RFID tags.

31. The system of claim 30, wherein:

the container comprises two or more container RFID tags; and the two or more container RFID tags and the one or more reader antennae provide redundancy such that the system electronics are configured to determine the rotational orientation of the container at the container location based on the results of the one or more reader antennae attempting to read the two or more container RFID tags, even if one of the container RFID tags fails.

32. The system of claim 30, wherein:

at least one container RFID tag wraps around a corner of the container; and at least one reader antennae wraps around a corner of the container location.

33. A system for storing samples, the system comprising:

a cabinet having a plurality of container locations, each container location configured to receive a container configured to store one or more samples, wherein:

each container is configured with a container RFID tag; and each container location is configured with a location RFID tag; and system electronics configured to support reading (i) each location RFID tag to enable the system to determine whether the system electronics is operating properly and (ii) each container RFID tag to identify the container location of each container stored in the cabinet, wherein:

the container comprises two or more container RFID tags;

the system electronics are configured to establish a logical grouping of the two or more container RFID tags for the container; and the system electronics are configured to use the logical grouping to determine when one of the reader antennae of the container location reads a container RFID tag of another container at another container location.

\* \* \* \* \*